(12) United States Patent
Homan et al.

(10) Patent No.: US 8,046,051 B2
(45) Date of Patent: Oct. 25, 2011

(54) METHOD AND APPARATUS FOR THE OBSERVATION OF A CATHETER WITHIN A VESSEL SYSTEM

(75) Inventors: Robert Johannes Frederik Homan, Eindhoven (NL); Drazenko Babic, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 969 days.

(21) Appl. No.: 11/909,466

(22) PCT Filed: Mar. 16, 2006

(86) PCT No.: PCT/IB2006/050818
§ 371 (c)(1),
(2), (4) Date: Sep. 24, 2007

(87) PCT Pub. No.: WO2006/103580
PCT Pub. Date: Oct. 5, 2006

(65) Prior Publication Data
US 2008/0171936 A1 Jul. 17, 2008

(30) Foreign Application Priority Data
Mar. 29, 2005 (EP) .................. 05102456

(51) Int. Cl.
*A61B 6/00* (2006.01)
(52) U.S. Cl. .................. 600/424; 600/426; 382/128
(58) Field of Classification Search .............. 600/426, 600/424, 427, 431, 434; 606/130
See application file for complete search history.

(56) References Cited

U.S. PATENT DOCUMENTS

| | | |
|---|---|---|
| 5,255,680 A | 10/1993 | Darrow et al. |
| 2002/0090058 A1 | 7/2002 | Yasuda et al. |
| 2003/0208116 A1 | 11/2003 | Liang et al. |
| 2004/0082854 A1 | 4/2004 | Essenreiter et al. |
| 2005/0015006 A1 | 1/2005 | Mitschke et al. |

FOREIGN PATENT DOCUMENTS

| | | |
|---|---|---|
| WO | 2003086190 A1 | 10/2003 |
| WO | 2004103198 A | 12/2004 |
| WO | 2005020148 A | 3/2005 |

OTHER PUBLICATIONS

Shirley A. M. Baert et al; "Three-Dimensional Guide-Wire Reconstruction From Biplane Image Sequences for Integrated Display in 3-D Vasculature", IEEE Transctions on Medical Imaging, vol. 22, No. 10, Oct. 2003, pp. 1252-1258.
Theo Van Walsum et al; "Guide Wire Reconstruction and Visualization in 3 DRA Using Monoplane Fluoroscooopic Imaging", IEEE Transactions on Medical Imaging, vol. 24, No. 5, May 2005.

*Primary Examiner* — Parikha S Mehta

(57) ABSTRACT

To observe a catheter (43) advancing in a vessel system, a 3D model of the vessel system is reconstructed with the help of differently oriented X-ray projections ($P_1^A, \ldots$) generated by a C-arm system (20) during the injection of a contrast agent. Next, a movement corridor (M) of the catheter (43) is determined from the 3D model. During an examination procedure, current projections (P) are generated showing an image (43') of the catheter that can be registered with the reconstructed 3D model and/or the movement corridor (M). Based on the registered catheter image and 3D model of the vessel geometry or the movement corridor (M), an optimal projection direction ($d_{opt}$) is determined and the C-arm system (20) is controlled to orient the next projections in the optimal projection direction.

18 Claims, 1 Drawing Sheet

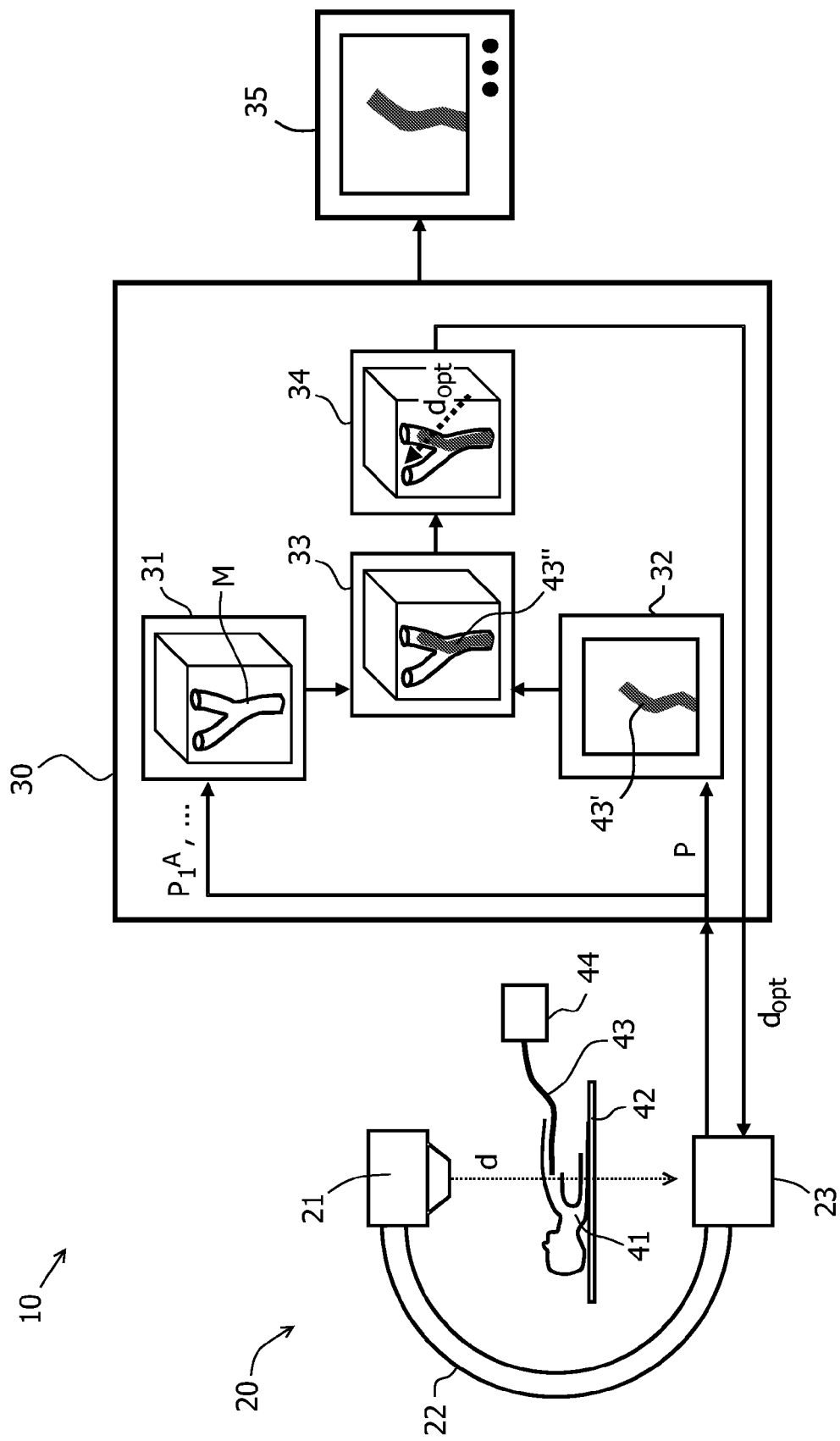

METHOD AND APPARATUS FOR THE OBSERVATION OF A CATHETER WITHIN A VESSEL SYSTEM

CROSS REFERENCE TO RELATED APPLICATIONS

This application claims the benefit of PCT application no. PCT/IB2006/050818 filed Mar. 16, 2006, which claims the benefit of EP application EP 05 102 456.0 filed Mar. 29, 2005, both of which are incorporated herein by reference.

FIELD OF THE INVENTION

The invention relates to an examination apparatus, a method and a record carrier for the observation of an instrument in a body volume, particularly a catheter in a vessel system.

BACKGROUND OF THE INVENTION

In radiological interventional procedures an instrument like a catheter is navigated through the body of a patient under continuous X-ray observation. The U.S. Pat. No. 5,255,680 describes for such procedures an examination apparatus that localizes the current position of the catheter tip with the help of radiofrequency markers and then positions the X-ray apparatus automatically in such a way that the catheter is always in the field of view. One disadvantage of this approach is the need of additional markers on the instruments. Moreover, the generated projections are often insufficient for the navigation of a catheter through a complicated vessel geometry.

SUMMARY OF THE INVENTION

Based on this situation it was an object of the present invention to provide means for a facilitated observation of an instrument in a body volume, particularly for the navigation of a catheter in the vessel system of a patient.

According to its first aspect, the invention relates to an examination apparatus for the observation of an instrument in a body volume. The instrument may for instance be a catheter, a guide wire, a biopsy needle, or an endoscope, and the instrument may particularly be moved in the vessel system of a (human or animal) body. The invention is however not restricted to medical applications. The examination apparatus comprises the following components:

a) An imaging device for generating projections of the body volume with an adjustable projection geometry. Said projections are called "current projections" in the following because they typically represent live-pictures in a (medical) examination procedure. In general the term "current" shall however not be limiting with respect to the time the projections are generated. The imaging device may preferably be a rotational X-ray device like a CT-scanner or a C-arm device (mono-plane or bi-plane). The adjustable projection geometry may typically comprise the projection direction and, moreover, the shape of the field of view and/or the source-image-distance.

b) A data processing unit that is connected to the imaging device and that may for example be a conventional computer with components like central processing unit, memory, I/O-interfaces and the like together with appropriate software. The data processing unit comprises the following components, which may be realized by dedicated hardware and/or software and/or data:

b1) A three-dimensional (3D) representation of a movement corridor of the instrument inside the body volume. The movement corridor comprises all spatial locations to which the instrument can (and shall) move or at which it can (and shall) reside. A typical example of a movement corridor is the part of the vessel system of a patient through which a catheter is moved to a target location. For biopsies the movement corridor is the planned path, because no natural movement corridor exist here. The 3D movement corridor is preferably created with the use of segmentation, path planning or path tracking algorithms or a combination thereof from a three-dimensional reconstruction of the body volume (e.g. CT, MR or 3DRX). The movement corridor can also be determined from a CT or MRI volume if this volume can be registered with a pre-interventional 3DRA volume (3D-3D registration) or with the interventional images (2D-3D registration).

b2) A localization module for determining the current location of the instrument with respect to the aforementioned 3D representation of the movement corridor, wherein said determination is preferably based on at least one current projection generated by the imaging device (for this reason, the determined location is called "current location" in the following). If the actual projection geometry of the imaging device and the relative location of the 3D representation with respect to the imaging device are known, the determination of the current location is usually a straightforward calculation. Appropriate methods for this step may be found in literature (e.g. for bi-plane images: "3D Guide wire reconstruction from biplane image sequence for integrated display in 3D vasculature", IEEE Transactions on Medical Imaging, Vol. 22, No. 10, pp. 1252-1258, 2003; for mono-plane images: Th. van Walsum, S. A. M. Baert, W. J. Niessen: "Guide Wire Reconstruction and Visualization in 3DRA using Monoplane Fluoroscopic Imaging", IEEE Transactions on Medical Imaging, 2005). The determination of the current location of the instrument with respect to the 3D representation of the movement corridor may alternatively be based on technologies of (catheter) navigation, for example on the use of radiofrequency markers that measure the three-dimensional position of the instrument.

b3) A steering module for making the imaging device assume an optimal projection geometry with respect to the current location of the instrument. The definition of an "optimal projection geometry" is typically based on criteria pre-defined by the user. Examples for such criteria are described in connection with preferred embodiments of the invention. The determination of the optimal projection geometry may particularly take into account the course of the movement corridor in the neighborhood of the instrument.

The examination apparatus described above has the advantage to provide live projections of an instrument in a body volume automatically with an optimal projection geometry. Thus the navigation of the instrument can be done faster and under a better visual control than with conventional devices which produce only projections from a constant direction and/or require a manual adaptation of the projection geometry.

According to a further development of the invention, the examination apparatus comprises an injection device for injecting a contrast agent into the vessel system of a patient. Said injection device may for example comprise a syringe with an automatic pump for a controlled delivery of contrast agent. The possibility to inject contrast agent allows the generation of angiographic projections that show the vessels with high contrast.

The data processing unit preferably comprises also a reconstruction module for reconstructing a 3D model of the body volume from differently oriented projections of the body volume, wherein the movement corridor of the instrument can be determined, tracked or planned from said volume. While said 3D model may in principle originate from any suitable source (e.g. MRI), it is preferably generated using the imaging device of the examination apparatus. The reconstruction module may apply any of the various known reconstruction algorithms for the determination of the 3D model from projections, for example Algebraic Reconstruction Technique (ART) or Maximum Likelihood (ML) approaches. The determination of the movement corridor from the reconstructed 3D model can be done manually or with any of the various known algorithms of (vessel-) segmentation or path tracking.

It was already mentioned that the optimal projection geometry can be determined with different user-defined criteria. According to a preferred embodiment, the optimal projection direction is determined such that it is at least approximately perpendicular to the course of the corridor section in which the instrument is located currently or subsequently (i.e. after the next forward movement). In vascular interventions, this corridor section corresponds to the vessel section in which the catheter tip resides. Projecting this section from a direction perpendicular to its axis will then guarantee an optimal representation without perspective foreshortening.

In a further development of the aforementioned embodiment, the optimal projection direction is chosen to deviate from an (exactly) perpendicular direction relative to a corridor section to such an amount that said corridor section is separated in the resulting projection images from other corridors sections. If the current vessel section of a catheter is for example occluded by other vessels, the projection direction may be changed from the perpendicular direction to admit a better view with reduced occlusions.

The data processing unit may further comprise a module for (automatically or interactively with inputs from a user) determining a path through the movement corridor that leads from a given starting location to a given target location. In catheter interventions, the starting location may for example be given by the insertion through which the catheter is introduced into the body of a patient, while the target location is the defect that shall be treated or diagnosed.

In a further development of the aforementioned embodiment, the data processing unit comprises additionally a simulation module for calculating in advance the optimal projection geometries with respect to the whole determined path through the movement corridor or at least a part of this path. This calculation may take further optimization criteria into account, for example a minimization of the necessary movements of the imaging device (e.g. a C-arm). During an intervention, the pre-calculated optimal projection geometries can then simply be recalled from a memory according to the current location of the instrument. Preferably the simulation module also allows a representation of the calculated virtual procedure on a screen. A C-arm may for example be presented on the screen following the planned path, combined with the corresponding projection view on the volume. A physician may then decide if the planned procedure is feasible and manually correct it if necessary.

The invention further relates to a method for the observation of an instrument in a body volume which comprises the following steps:

The determination of a three-dimensional representation of a movement corridor of the instrument inside the body volume. The representation may particularly be derived (e.g. tracked, segmented, or manually determined) from a 3D model of the body volume that is reconstructed from differently oriented projections of the body volume.

The generation of at least one current projection of the body volume. Said projection may for example be generated by a rotational X-ray device. In bi-plane systems, two current projections are available for each point in time.

The determination of the current location of the instrument with respect to the 3D representation, wherein this determination is preferably based on the current projection.

The determination of an optimal projection geometry with respect to the current location of the instrument.

An additional step of the method may particularly be the generation of a new projection of the body volume with the determined optimal projection geometry.

The method comprises in general form the steps that can be executed with an examination apparatus of the kind described above. Therefore, reference is made to the preceding description for more information on the details, advantages and improvements of that method.

Finally, the invention comprises a record carrier, for example a floppy disk, a hard disk, or a compact disc (CD), on which a computer program for the observation of an instrument in a body volume is stored, wherein said program is adapted to execute a method of the aforementioned kind.

These and other aspects of the invention will be apparent from and elucidated with reference to the embodiment(s) described hereinafter.

BRIEF DESCRIPTION OF THE DRAWINGS

In the following the invention is described by way of example with the help of the accompanying single drawing which schematically shows an examination apparatus according to the present invention.

DESCRIPTION OF PREFERRED EMBODIMENTS

A major part of the radiological interventional procedures of today, whether being vascular or nonvascular, is based on real-time X-ray guidance of endovascular devices through human vessels or hollow anatomical structures. When spoken about the vessel intervention in particular, the interventional target is a successful repair of vessel pathology via non-invasive intra-arterial or intra-venous approach. In order to achieve the target, the interventional radiologist is supposed to have an appropriate angio machine at his disposal, which is able to produce real-time angio images of the vessel anatomy. However, even the most advanced angio machines of today suffer from multiple shortcomings, when used for the interventional guidance. One of the most inconvenient shortcomings of the state of the art angio machines is their 2D projection image nature, which does not allow for enhanced understanding of vessel mutual relationship.

Although the recently developed 3D angio reconstruction technique, based on the so-called rotational angiography method, resolved some of the 2D projections drawbacks, there are some remaining unsolved issues that require further improvements. Thus both monoplane and biplane angio systems provide either static or dynamic imaging from one or two incidences. When needed, the C-arm geometry can be removed to another incidence in order to appreciate vessel tree and the pathology from different projection angle. In a case of multiple vessel superimposition and complex vessel anatomy, the C-arm should be removed to different incidence frequently in order to follow a curved vessel course. This is considered to be labor intensive, time consuming and provides non-optimal vessel projection (human inability to position the C-arm perpendicular to the vessel axis or at least to the most optimal projection). The biplane angio systems provide simultaneous display from two channels, which gives double as much information as the monoplane angio machines, but again two non-optimal vessel projections.

The present invention tries to overcome the aforementioned problems with an approach that couples the orientation of the rotational X-ray device to the position of the instrument. This approach is described in more detail below with respect to a catheter intervention.

The examination apparatus 10 shown in the FIGURE comprises a rotational X-ray device 20 and a data processing unit 30 coupled thereto. The rotational X-ray device is particularly a C-arm system 20 with an X-ray source 21 and an X-ray detector 23 that are coupled via a rotatable C-arm 22. A patient 41 is lying on a patient table 42 in the rotational centre of the C-arm system 20. The imaging device may thus generate X-ray projections of the patient 41 from various projection directions d.

The FIGURE further illustrates a catheter 43 which is advanced through the vessel system of the patient 41 to a target location that shall be treated or diagnosed. The catheter 43 is coupled to an injection device 44 by which a bolus of contrast agent may be injected for a contrasted imaging of the vessels.

The data processing system 30 (workstation) is bidirectionally coupled to the rotational X-ray device 20 and comprises several logical modules which are typically realized by a combination of hardware, software and data. These modules are described in the following.

A reconstruction module 31 of the data processing unit 30 is adapted to receive a series of differently oriented angiographic projections $P_1^A, \ldots$ generated by the X-ray device 20 during an injection of contrast agent. Moreover, it is adapted to reconstruct a three-dimensional model of the vessel system from these projections $P_1^A, \ldots$ with the help of known algorithms (e.g. ART, ML). The three-dimensional vessel reconstruction is used for determination of the vessel to be catheterized (entry point) and the pathology to be treated (target point). Both the points may be connected with the automated vessel analysis software (3DRA functionality) that can trace a path or a representation M of a "movement corridor" to be followed by a catheter.

A module 32 receives a "current" (or "online", "live") projection P generated with the current projection geometry d of the X-ray device 20 (or two projections in case of a bi-plane system). This current projection P shows the projection image 43' of the catheter 43, while the vessels can normally not be seen without the injection of contrast agent.

A localization module 33 determines the location of the catheter or its tip in the current projection P and registers this 2D location with the 3D representation M, i.e. it finds the location 43" in the 3D representation M that corresponds to the projection image 43' of the catheter. Such a registration may for example be based on the known projection geometries of the volume projections $P_1^A, \ldots$ and the current projection P (provided that the patient 41 has not moved in the meantime). The automatic determination of the catheter tip will take place as soon as the catheter reaches the entry point inside the 3D reconstructed volume. The tip will be highlighted and back-projected into the 3D space.

In the next step, a steering module 34 determines an optimal projection direction $d_{opt}$ for the current location of the catheter tip (or of the whole catheter or any other catheter section of interest). The optimal projection direction $d_{opt}$ is typically perpendicular to the vessel axis at the tip of the catheter (or the axis of the vessel section in front of the tip which will be entered next) in order to map said section of the vessel without foreshortening.

The steering module 34 sends the determined optimal projection direction $d_{opt}$ as command to the X-ray device 20 which then rotates to assume this direction. The next live projection image generated by the X-ray device 20 will then show the catheter and the surrounding vessels from an optimal focus. The position of the catheter tip will thus be followed by automatic C-arm movement in such a way that the C-arm always positions itself perpendicular to the predefined path. When multiple vessels are superimposed on each other, the C-arm may slightly deviate from the ideal path in order to visualize the vessel in question appropriately.

According to a variant of the procedure described above, the data processing unit 30 comprises a simulation module (which may for instance be integrated into module 31) that determines and stores optimal projection geometries in advance for the whole movement corridor M (or at least for the whole planned path of the catheter 43). These geometries may then take "global" criteria concerning the whole catheter trajectory into account, for example a minimization of the associated C-arm movement during the whole procedure. During the intervention, module 34 then only needs to recall the predetermined projection geometries according to the current localizations 43" of the catheter.

The data processing unit 30 is further coupled to a monitor 35 on which images can be displayed, for example the reconstructed 3D volume, the 3D movement corridor M, the current projection P, the registered combination of movement corridor and current projection, or a simulated intervention with associated C-arm configurations and simulated (optimal) projection views.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. An examination apparatus for the observation of a catheter during advancement through a vessel system of a patient, the apparatus comprising:
   an injection device which injects a contrast agent into the vessel system;
   a rotational arm imaging device which generates 2D projections of a volume of the patient containing a portion of the vessel system;
   a data processing unit connected to the imaging device and programmed to perform the processing steps of:
      reconstructing a 3D representation of the portion of the vessel system from the 2D projections generated by the imaging device when a contrast agent was present in the vessel system;
      locating and registering a current 2D projection of the catheter in the vessel system generated in a current projection direction with the 3D representation of the vessel system,
      displaying on a monitor an image of the registered current 2D projection and the 3D representation of the portion of the vessel system,
      determining an optimal projection direction for generating a next 2D projection of the catheter, and
      controlling the rotational arm imaging device to rotate to the determined optimal projection direction before generating the next 2D projection of the catheter.

2. The examination apparatus according to claim 1, wherein when the catheter is advancing through a first section of the vessel system approaching another section of the vessel system in which the vessel branches into at least first and second branches, the determined optimal projection direction being a direction substantially perpendicular to a plane of the first and second branches.

3. The examination apparatus according to claim 1, wherein when the catheter is advancing through a vessel approaching a section of the vessel system in which the vessel branches into at least first and second branches, the optimal projection direction being a direction in which the first and second branches are displayed side-by-side such that the vessel branches are not superimposed.

4. The examination apparatus according to claim 1, wherein the optimal projection direction is one in which a vessel through which the catheter is advancing is not superimposed on another vessel.

5. The examination apparatus according to claim 1, wherein determining the optimum projection direction includes optimizing minimizing foreshortening of a tip of the catheter, minimizing superimposition of a vessel through which the catheter is advancing with other vessels, and minimizing the rotation of the arm of the rotational arm imaging device.

6. The examination apparatus according to claim 1, wherein the optimal projection direction ($d_{opt}$) is at least approximately perpendicular to a section of the vessel in which the catheter is currently or subsequently planned to be located.

7. The examination apparatus according to claim 6, wherein the optimal projection direction ($d_{opt}$) deviates from perpendicular such that the section of the vessel in which the catheter is currently or subsequently planned to be located is separated in the 2D projection from other vessel sections.

8. The examination apparatus according to claim 1, wherein the data processing unit is further programmed to perform the step of:
determining a path through the vessel system depicted in the 3D representation leading from a starting location to a target location.

9. The examination apparatus according to claim 8, wherein the data processing unit is further programmed to perform the step of:
calculating the optimal projection directions for a plurality of locations along the determined path from the 3D representation prior to advancing the catheter through the vessel system.

10. An examination apparatus for observing advancement of an instrument in a body volume, the apparatus comprising:
an imaging device which generates projections of the instrument in the body volume from each of a plurality of projection directions,
a data processing unit connected to the imaging device, the data processing unit performing the steps of:
locating and registering a current one of the projections of the instrument in the body with a 3D representation depicting in three dimensions at least a movement corridor along which the instrument is advanced in the body volume;
determining a next projection direction for a next projection based on the registered current projection and 3D representation, and
controlling the imaging device to generate the next projection along the determined next projection direction.

11. The examination apparatus according to claim 10, wherein the instrument includes one of a catheter, a guidewire, a biopsy needle, and an endosocope.

12. The examination apparatus according to claim 10, wherein the imaging device includes a rotational x-ray device and wherein the processing unit controls the imaging device to rotate to the next projection direction prior to generating the next projection.

13. The examination apparatus according to claim 12, wherein the data processing unit further forms the step of:
reconstructing the 3D representation from a plurality of the projections generated by the rotational x-ray device; and
segmenting the movement corridor from the 3D representation such that the 3D representation depicts the motion corridor in three dimensions.

14. The examination apparatus according to claim 10, wherein the data processing unit further performs the step of:
determining a path through the movement corridor leading from a selected starting location to a selected target location.

15. The examination apparatus according to claim 10, wherein the movement corridor is a vessel system and the apparatus is advanced through the vessel system, and wherein the next projection direction is determined by calculating at least one of:
optimal projection directions for each of a plurality of locations along the vessel system;
determining a direction perpendicular to a section of the motion corridor in which the instrument is located;
determining a direction in which foreshortening of a tip of the instrument is minimized;
minimizing movement of the imaging device; and
avoiding superimposition of a section of the motion corridor in which the instrument is currently located and other sections of the motion corridor.

16. A method for observing an instrument advancing in a body volume, the method comprising:
generating a current 2D projection with an imaging device of the instrument in the body cavity;
localizing and registering the current 2D projection with a 3D representation depicting in three dimensions at least a movement corridor along with the instrument is advanced in the body cavity;
determining a next projection direction for a next projection based on at least one of the 2D projection and the 3D representation;
controlling the imaging device to generate the next projection in the determined next projection direction.

17. The method according to claim 16, further including:
displaying the current projection and the 3D representation on a display device; and
advancing the instrument in accordance with the displayed projection and the 3D representation.

18. A non-transitory computer-readable medium which carries software configured to control one or more processors to perform a method comprising the steps of:
generating a current 2D projection with an imaging device of the instrument in a body cavity;
localizing and registering the current 2D projection with a 3D representation depicting in three dimensions at least a movement corridor along which the instrument is advanced in the body cavity;
determining a next projection direction for a next projection based on at least one of the 2D projection and the 3D representation;
controlling the imaging device to generate the next projection in the determined next projection direction.

* * * * *